United States Patent
Acker et al.

(10) Patent No.: US 10,342,948 B2
(45) Date of Patent: *Jul. 9, 2019

(54) THERAPEUTIC GAS DELIVERY DEVICE WITH PULSED AND CONTINUOUS FLOW CONTROL

(71) Applicant: Mallinckrodt Hospital Products IP Limited, Mulhuddart (IE)

(72) Inventors: Jaron Acker, New York, NY (US); Thomas Kohlmann, McFarland, WI (US); Craig R. Tolmie, Stoughton, WI (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 730 days.

This patent is subject to a terminal disclaimer.

(21) Appl. No.: 14/218,067

(22) Filed: Mar. 18, 2014

(65) Prior Publication Data

US 2014/0261415 A1    Sep. 18, 2014

Related U.S. Application Data

(60) Provisional application No. 61/802,798, filed on Mar. 18, 2013.

(51) Int. Cl.
*A61M 16/12*    (2006.01)
*A61M 16/20*    (2006.01)
(Continued)

(52) U.S. Cl.
CPC ........ *A61M 16/12* (2013.01); *A61M 16/0677* (2014.02); *A61M 16/202* (2014.02);
(Continued)

(58) Field of Classification Search
CPC ........ A61M 16/12–127; A61M 16/203; A61M 2205/3334
See application file for complete search history.

(56) References Cited

U.S. PATENT DOCUMENTS 4,584,996 A    4/1986  Blum
4,686,974 A *  8/1987  Sato ............... A61M 16/00
                                              128/204.23
(Continued)

FOREIGN PATENT DOCUMENTS

DE    10-2010-016699    11/2011
EP         0659445        6/1995
(Continued)

OTHER PUBLICATIONS

PCT International Search Report and Written Opinion in PCT/US2014/028483, dated Oct. 16, 2014, 18 pages.
(Continued)

*Primary Examiner* — Valerie L Woodward
(74) *Attorney, Agent, or Firm* — Servilla Whitney LLC (57) ABSTRACT

Described are methods and devices for therapeutic or medical gas delivery that utilize at least one proportional control valve and at least one binary control valve. The proportional control valve may be in series with the binary control valve to provide a valve combination capable of pulsing therapeutic gas at different flow rates, depending on the setting of the proportional control valve. Alternatively, the proportional control valve and binary control valve may be in parallel flow paths.

18 Claims, 2 Drawing Sheets

(51) Int. Cl.
*A61M 16/06* (2006.01)
*A61M 16/00* (2006.01)

(52) U.S. Cl.
CPC ... *A61M 16/203* (2014.02); *A61M 2016/0021* (2013.01); *A61M 2016/0027* (2013.01); *A61M 2016/0039* (2013.01); *A61M 2202/0275* (2013.01); *A61M 2205/3334* (2013.01); *A61M 2205/502* (2013.01)

(56) References Cited

U.S. PATENT DOCUMENTS

| | | | |
|---|---|---|---|
| 5,423,313 A * | 6/1995 | Olsson | A61M 16/00 128/203.14 |
| 5,558,083 A | 9/1996 | Bathe et al. | |
| 5,732,693 A | 3/1998 | Bathe et al. | |
| 5,752,504 A | 5/1998 | Bathe | |
| 5,918,596 A * | 7/1999 | Heinonen | A61M 16/12 128/204.21 |
| 6,125,846 A | 10/2000 | Bathe et al. | |
| 6,131,572 A * | 10/2000 | Heinonen | A61M 16/12 128/204.22 |
| 6,581,599 B1 * | 6/2003 | Stenzler | A61M 16/12 128/203.12 |
| 6,962,154 B2 | 11/2005 | Krebs | |
| 7,523,752 B2 | 4/2009 | Montgomery et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,431,163 B2 | 4/2013 | Baldassarre et al. | |
| 8,573,209 B2 | 11/2013 | Bathe et al. | |
| 8,573,210 B2 | 11/2013 | Bathe et al. | |
| 8,776,794 B2 | 7/2014 | Bathe et al. | |
| 8,776,795 B2 | 7/2014 | Bathe et al. | |
| 8,795,741 B2 | 8/2014 | Baldassarre | |
| 8,846,112 B2 | 9/2014 | Baldassarre | |
| 9,616,193 B2 | 4/2017 | Acker et al. | |
| 2002/0185126 A1 * | 12/2002 | Krebs | A61M 16/12 128/200.24 |
| 2013/0087145 A1 * | 4/2013 | Kobrich | A61M 16/12 128/203.14 |
| 2013/0098361 A1 | 4/2013 | Kobrich et al. | |
| 2014/0076321 A1 | 3/2014 | Hendrickx et al. | |

FOREIGN PATENT DOCUMENTS

| | | |
|---|---|---|
| WO | WO-99/22796 | 5/1999 |
| WO | WO-99/59662 | 11/1999 |
| WO | WO-2012/153293 | 11/2012 |

OTHER PUBLICATIONS

PCT Invitation to Pay Additional Fees Annex Communication Relating to the Results of the Partial International Search in PCT/US2014/028483, dated Jul. 30, 2014, 6 pages.
INOmax DS (Delivery System): Operation Manual (800 ppm INOMAX (nitric oxide) for Inhalation), Ikaria, Inc. 2010, 112 pages.
INOmax DSIR (Delivery System): Operation Manual (800 ppm INOMAX (nitric oxide) for Inhalation), Ikaria, Inc. 2012, 136 pages.
INOvent Delivery System: Operation and Maintenance Manual (CGA Variant), Datex-Ohmeda, Inc. 2000, 180 paqes.
Using the INOpulse DS Subject Guide, Ikaria, Inc. 2012, 50 pages.
INOmax Label, (Nitric Oxide) for Inhalation, 2009, 9 pages.
INOmax Label, Nitric Oxide Gas, INO Therapeutics, 2013, 2 pages.
Non-Final Office Action in U.S. Appl. No. 14/211,919 dated Jul. 5, 2016, 15 pages.
Non-Final Office Action in U.S. Appl. No. 15/483,138 dated Aug. 29, 2018, 19 pages.
PCT International Preliminary Report on Patentability in PCT/US2014/028483 dated Sep. 24, 2015, 11 pages.

* cited by examiner

THERAPEUTIC GAS DELIVERY DEVICE WITH PULSED AND CONTINUOUS FLOW CONTROL

CROSS-REFERENCE TO RELATED APPLICATIONS

This application claims the benefit under 35 U.S.C. § 119(e) to U.S. Provisional Application No. 61/802,798, filed Mar. 18, 2013, the entire contents of which are incorporated herein by reference in their entirety.

TECHNICAL FIELD

Embodiments of the present invention generally relate to the field of therapeutic gas administration, particularly to devices and methods for nitric oxide delivery.

BACKGROUND

Nitric oxide (NO) is a gas that, when inhaled, acts to dilate blood vessels in the lungs, improving oxygenation of the blood and reducing pulmonary hypertension. Because of this, nitric oxide is provided as a therapeutic gas in the inspiratory breathing gases for patients with pulmonary hypertension.

Some nitric oxide delivery devices utilize a proportional control valve to continuously flow therapeutic gas to provide an approximately constant concentration of nitric oxide in the patient's inspiratory breathing gas, based on a desired concentration set by a clinician. However, as the flow rate of breathing gas rapidly rises and falls within the inspiratory or expiratory phases, it becomes difficult to continuously provide a proportional ratio-metric dose of delivered NO gas dependent on inspired flow. This is particularly true at the low end of the NO flow range, such as when the NO set dose and ventilator flow rates result in a low NO demand and therefore a low therapeutic gas demand.

Other nitric oxide delivery devices utilize one or more binary control valves to approximate an average constant concentration of nitric oxide by constantly pulsing through the binary control valves. These devices also have problems at the low end of the NO delivery range, and may have problems with response time when meeting the sudden increased NO flow demand in response to a ventilator inspiratory phase.

Still other nitric oxide delivery devices administer a single pulse of nitric oxide to the patient as the patient inhales spontaneously. Such devices often use a pressure or flow sensor known as a patient trigger sensor to detect when a patient begins inspiration for a particular breath and also to detect each phase of the patients' breath: i.e. inspiratory, expiratory, etc. These devices will generally use at least one binary control valve to provide a constant flow of NO during the pulsing event, but have a limited dose range because dose amounts can only be varied by varying the time that the binary control valve is open.

Accordingly, there is a need for new methods and devices for delivery of therapeutic gases such as NO-containing gases.

SUMMARY

Provided are methods and devices that utilize at least one binary control valve (i.e. a constant flow valve) and at least one proportional control valve (i.e. a variable flow valve) to provide enhanced dosing ranges for therapeutic gas administration.

One aspect of the present invention relates to a therapeutic gas delivery device that comprises at least one binary control valve and at least one proportional control valve. In one or more embodiments of this aspect, the gas delivery device comprises an inlet to connect to a source of therapeutic gas, an outlet to connect to a device that introduces the therapeutic gas to a patient, at least one binary control valve in fluid communication with the inlet and outlet that delivers a constant flow of the therapeutic gas, at least one proportional control valve in fluid communication with the inlet and outlet that delivers a variable flow of the therapeutic gas, and a control system that delivers the therapeutic gas through one or more of the binary control valve and the proportional control valve. The therapeutic gas may comprise nitric oxide or a nitric oxide-releasing agent, or may be another therapeutic gas as described herein.

According to one or more embodiments, the binary control valve and the proportional control valve are in series. This combination of the binary control valve and the proportional control valve may provide pulses of therapeutic gas at varying flow rates. In some embodiments, the therapeutic gas delivery device further comprises a pressure sensor, wherein the proportional control valve is upstream of the pressure sensor and the pressure sensor is upstream of the binary control valve.

In one or more embodiments, the binary control valve and the proportional control valve are in parallel flow paths.

If multiple binary and/or proportional control valves are used, various combinations of valves in parallel and/or in series are possible. One particular configuration can include multiple binary control valves in parallel, which may provide pulses of therapeutic gas at either the same or different flow rates. In some embodiments, the ratio of the flow rate of the first binary control valve to the flow rate of the second binary control valve is in the range from about 1:2 to about 1:10. In some embodiments, the control system delivers multiple pulses per breath through one or more of the first binary control valve and the second binary control valve.

According to one or more embodiments, the gas control system delivers the therapeutic gas into a flow of breathing gas through one or more of the binary control valve and the proportional control valve to provide a combined flow of therapeutic gas and breathing gas with a substantially constant concentration of therapeutic gas. In further embodiments, the binary control valve and the proportional control valve are in parallel flow paths and the control system delivers a continuous flow of therapeutic gas through the proportional control valve when a therapeutic gas demand is greater than or equal to 5% of a delivery range and delivers one or more pulses of therapeutic gas through the binary control valve when the therapeutic gas demand is less than or equal to 1% of the delivery range. As described herein, other therapeutic gas demands may be used to determine whether a binary valve or proportional valve is used.

The device that introduces the therapeutic gas to the patient may be in fluid communication with a ventilator, or the patient may be breathing spontaneously. Examples of devices that may be used to introduce the therapeutic gas to the patient include a nasal cannula, endotracheal tube or a face mask.

In some embodiments, the control system provides a single pulse in a patient's breath through one or more of the binary control valve and the proportional control valve.

Another aspect of the present invention pertains to a therapeutic gas delivery device that comprises a binary control valve and a variable pressure regulator. In various embodiments of this aspect, the therapeutic gas delivery device comprises an inlet to connect to a source of therapeutic gas, an outlet to connect to a device that introduces the therapeutic gas to a patient, at least one binary control valve in fluid communication with the inlet and outlet that delivers a constant flow of the therapeutic gas when the upstream pressure is constant, at least one variable pressure controller in fluid communication with the binary control valve that varies the pressure upstream of the binary control valve, and a control system that delivers the therapeutic gas through the binary control valve. The therapeutic gas may comprise nitric oxide or a nitric oxide-releasing agent.

According to one or more embodiments, the control system is in communication with the variable pressure regulator and varies the pressure upstream of the binary control valve. In some embodiments, the variable pressure controller comprises a proportional control valve and a pressure sensor.

As with other embodiments described herein, the system may comprise multiple binary control valves, multiple proportional control valves and/or multiple variable pressure regulators. In some embodiments, the delivery system comprises a second binary control valve in parallel to the first binary control valve. These two binary control valves may provide pulses of therapeutic gas at either the same or different flow rates. In some embodiments, the ratio of the flow rate of the first binary control valve to the flow rate of the second binary control valve is in the range from about 1:2 to about 1:10. In some embodiments, the control system delivers multiple pulses per breath through one or more of the first binary control valve and the second binary control valve.

Again, the device that introduces the therapeutic gas to the patient may be in fluid communication with a ventilator, or the patient may be breathing spontaneously. Examples of devices that may be used to introduce the therapeutic gas to the patient include a nasal cannula, endotracheal tube or a face mask.

In some embodiments, the control system provides a single pulse in a patient's breath.

Yet another aspect of the present invention a method of administering a therapeutic gas to a patient comprising using any of therapeutic delivery devices described herein. In some embodiments, the method comprises providing a therapeutic gas delivery device having at least one binary control valve that delivers a constant flow of therapeutic gas and at least one proportional control valve that delivers a variable flow of the therapeutic gas and delivering therapeutic gas to the patient during inspiration through one or more of the binary control valve and the proportional control valve. As with any of the embodiments described herein, the therapeutic gas includes, but is not limited to, nitric oxide or a nitric oxide-releasing agent.

In one or more embodiments, the binary control valve and the proportional control valve are in series such that the combination of the binary control valve and the proportional control valve may provide pulses of therapeutic gas at varying flow rates.

In one or more embodiments, the binary control valve and the proportional control valve are in parallel flow paths.

Various embodiments provide that the therapeutic gas is delivered so that the patient is administered a constant concentration of drug. For example, the method may further comprise measuring a flow of breathing gas and delivering the therapeutic gas in an amount substantially proportional to the flow of breathing gas.

In some embodiments, the binary control valve and the proportional control valve are in parallel flow paths and a continuous flow of therapeutic gas is delivered through the proportional control valve when a therapeutic gas demand is greater than or equal to 5% of a delivery range and one or more pulses of therapeutic gas is delivered through the binary control valve when the therapeutic gas demand is less than or equal to 1% of the delivery range.

In one or more embodiments, the therapeutic gas delivery device further comprises a second binary control valve in parallel to the first binary control valve, which may deliver constant flow or pulses of therapeutic gas at the same or different flow rates. In some embodiments, the ratio of the flow rate of the first binary control valve to the flow rate of the second binary control valve is in the range from about 1:2 to about 1:10.

One or more embodiments provide that the method further comprises sensing the beginning of the patient's inspiration and delivering one or more pulses of therapeutic gas to the patient during inspiration. In some embodiments, at least one pulse is delivered in the first half of the patient's inspiration.

In one or more embodiments, a first amount of therapeutic gas is delivered to the patient in a first breath, and the method further comprises monitoring the patient's respiratory rate or changes in the patient's respiratory rate and varying the quantity of therapeutic gas delivered to the patient in one or more subsequent breaths based on the monitored respiratory rate or changes in the patient's respiratory rate.

The foregoing has outlined rather broadly certain features and technical advantages of the present invention. It should be appreciated by those skilled in the art that the specific embodiments disclosed may be readily utilized as a basis for modifying or designing other structures or processes within the scope present invention. It should also be realized by those skilled in the art that such equivalent constructions do not depart from the spirit and scope of the invention as set forth in the appended claims.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Although specific reference is made to nitric oxide delivery devices, it will be understood by a person having ordinary skill in the art that the methods and devices described herein may be used to deliver other medical or therapeutic gases. Exemplary gases that may be administered include, but are not limited to, nitric oxide, oxygen, nitrogen, and carbon monoxide. As used herein, the phrase "therapeutic gas" refers to gas used to treat diseases or medical disorders in a patient.

If nitric oxide is used as the therapeutic gas, exemplary diseases or disorders that may be treated include persistent pulmonary hypertension of the newborn (PPHN), pulmonary arterial hypertension (PAH), chronic obstructive pulmonary disease (COPD), bronchopulmonary dysplasia (BPD), chronic thromboembolic pulmonary hypertension (CTE), idiopathic pulmonary fibrosis (IPF), acute respiratory distress syndrome (ARDS) or pulmonary hypertension (PH), or nitric oxide may be used as an antimicrobial agent.

Provided are methods and devices for administering therapeutic gas to a patient that utilize both binary and proportional control valves. These devices can provide enhanced dose ranges for both continuous constant concentration delivery and single pulse per breath delivery.

As used herein, a "binary control valve" refers to a control valve having at least two states, the first state being completely closed and the second state being substantially open. Examples of such valves include, but are not limited to, solenoid valves and piezoelectric valves. Binary valves with large flow-through opening area (low pressure drop) to small diameter orifice (high pressure drop) are envisioned. Such valves generally provide a constant flow of gas when open, depending on the upstream pressure. In combination with a pressure regulator, these valves can provide a known, constant flow rate or pulsed volume of gas in proportion to the upstream pressure.

A "proportional control valve" as used herein is a valve that can provide a variable flow rate of gas. Unlike a binary control valve, a proportional control valve can have a variable opening to provide an almost infinite number of flow rates between the completely closed state and the completely open state. Over some portion of the control range these valves act in a linear region of flow output verses current input. They can be configured to control flow or pressure depending on the integration of the sensing device.

Accordingly, one aspect of the present invention relates to a therapeutic gas delivery device having at least one binary control valve and at least one proportional control valve. The binary control valve may be in series with the proportional control valve, or it may be in parallel with the proportional control valve. If more than one binary control valve and/or proportional control valve is present, the various valves may be arranged in multiple configurations with combinations of valves in series and in parallel.

Figure 1:
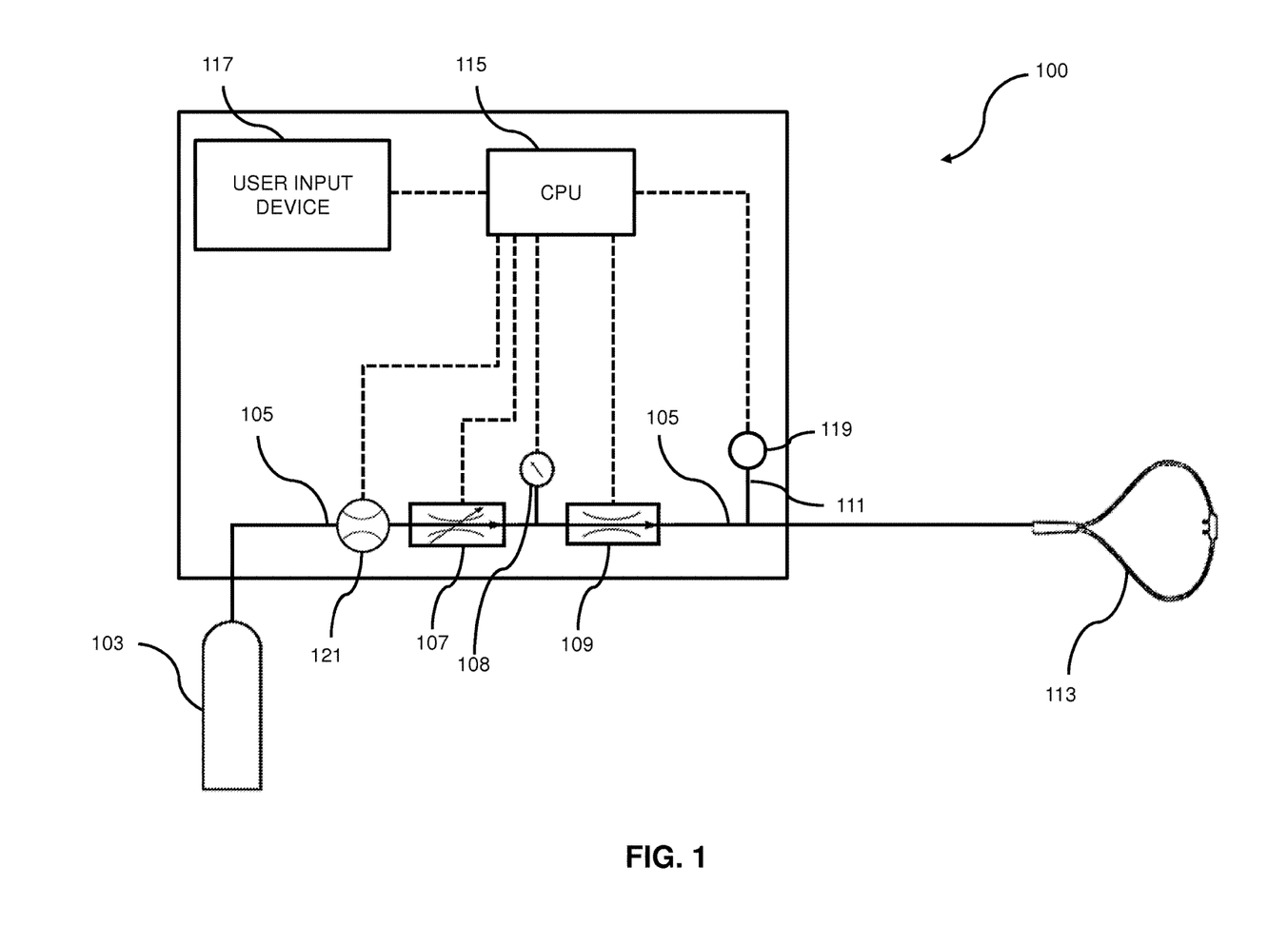
FIG. 1 illustrates a therapeutic gas delivery device having a proportional control valve and a binary control valve in series in accordance with one or more embodiments of the present invention.

FIG. 1 shows an exemplary nitric oxide delivery device 100 having the binary and proportional control valves in series. A source of therapeutic gas containing nitric oxide may include gas storage cylinder 103. Exemplary cylinders may contain NO in a carrier gas such as nitrogen, with a NO concentration ranging from 1 ppm to 20,000 ppm, such as from 5 ppm to 10,000 ppm, or from 10 ppm to 5,000 ppm. In one or more embodiments, the cylinder has a high nitric oxide concentration, such as about 2440 ppm or about 4880 ppm. In other embodiments, the cylinder concentration is about 800 ppm.

Instead of a cylinder storing gas comprising NO, a nitric oxide-releasing agent such as nitrogen dioxide ($NO_2$) or a nitrite salt ($NO_2^-$) may be used with appropriate reducing agents or co-reactants to provide a flow of NO. For example, gas storage cylinder 103 could contain $NO_2$ gas in a concentration ranging from 1 ppm to 20,000, and the device can utilize an appropriate reaction to convert the $NO_2$ to NO before administering to the patient.

Gas storage cylinder 103 is in fluid communication with conduit 105, which carries the therapeutic gas from gas storage cylinder 103 to the nitric oxide delivery device. The conduit 105 may be in fluid communication with a nasal cannula or other nasal or oral breathing apparatus 113 for delivering the therapeutic gas to the patient. In addition, conduit 105 may comprise a gas hose or tubing section, a pressure regulator, a delivery manifold, etc. Although specific reference is made to nasal cannulas, other types of nasal or oral breathing apparatuses may be used, such as breathing masks or endotracheal tubes.

One or more proportional control valves 107 regulate the flow of therapeutic gas through the conduit 105 to the patient, as well as one or more binary control valves 109. Although proportional control valve 107 is shown upstream of binary control valve 109 in FIG. 1, having the binary control valve 109 upstream of and in series with the proportional control valve 107 would be an equivalent configuration. In some embodiments, if the proportional control valve 107 is pressure-assisted open, it may need to be upstream of the binary control valve 109.

In addition to or as an alternate to the proportional control valve 107, a variable pressure regulator may be placed upstream of the binary control valve 109. A variable pressure regulator may act to control or maintain a known volume at a fixed pressure. Such a variable pressure regulator can vary the output pressure, thus varying the flow rate of the downstream binary control valve 109 and extending the dynamic range of the binary control valve 109. The variable pressure regulator may be electronically controlled by the control system of the nitric oxide delivery device.

In some embodiments, a pressure sensor 108 may be placed downstream of the proportional control valve 107 and upstream of the binary control valve 109. The combination of the proportional control valve 107 and the pressure sensor 108 may act as a variable pressure regulator to control pressure upstream of the binary control valve 109 because the proportional control valve 107 may control input flow to achieve the desired pressure at pressure sensor 108.

In some embodiments, a "known compressed gas volume" is measured by the pressure sensor 108 upstream of the binary control valve 109. In FIG. 1, the known compressed gas volume would be the volume of compressed gas in conduit 105 between the proportional control valve 107 and binary control valve 109. The portion of conduit 105 downstream from proportional control valve 107 and upstream of binary control valve 109 defines a chamber, and knowing the volume and pressure of this chamber allows the proportional control valve 107 to control the flow rate through the binary control valve 109.

A passageway 111 is in fluid communication with the conduit 105 which connects a patient trigger sensor 119 to the conduit 105. The patient trigger sensor 119 is a pressure or flow sensor. The signal from the trigger sensor 119 may be further processed via hardware and/or software logic by a control system comprising a central processing unit (CPU)

115. The trigger sensor 119 detects when a patient begins inspiration and/or expiration, and may provide that information to the control system.

In some embodiments, the trigger sensor 119 may be used to determine the patient's inspiration by detecting a negative pressure caused by the patient's breathing effort. This negative pressure may be measured between two reference points, such as between the passageway 111 and a differential pressure port on the nitric oxide delivery device (not shown). As passageway 111 is in fluid communication with the conduit 105, which in turn is in fluid communication with the patient, the pressure in passageway 111 will drop when a small sub atmospheric pressure in the patient's nose or mouth is created as the patient begins inspiration.

Similarly, the patient trigger sensor 119 may detect the patient's expiration by detecting a positive pressure caused by the patient. In some embodiments, this positive pressure differential is the amount by which the pressure in passageway 111 exceeds the pressure at the differential pressure port.

The nitric oxide delivery device 100 may comprise a control system including one or more CPUs 115. The CPU 115 may be in communication with a user input device 117. This user input device 117 can receive desired settings from the user, such as the patient's prescription (in mg/kg ideal body weight, mg/kg/hr, mg/kg/breath, mL/breath, cylinder concentration, delivery concentration, pulse duration, etc.), the patient's age, height, sex, weight, etc. In one or more embodiments, user input device 117 comprises a display and a keyboard and/or buttons, or may be a touchscreen device.

The CPU 115 may also be in communication with a flow sensor 121, which measures the flow of therapeutic gas through proportional control valve 107 and binary control valve 109. The CPU 115 can be coupled to a memory (not shown) and may be one or more of readily available memory such as random access memory (RAM), read only memory (ROM), flash memory, compact disc, floppy disk, hard disk, or any other form of local or remote digital storage. Support circuits (not shown) can be coupled to the CPU 115 to support the CPU 115, sensors, control valves, etc. in a conventional manner. These circuits include cache, power supplies, clock circuits, input/output circuitry, subsystems, power controllers, signal conditioners, and the like.

The CPU 115 of control system may be in communication with the proportional control valve 107, the binary control valve 109, the patient trigger sensor 119, the flow sensor 121 and the pressure sensor 108. When the patient trigger sensor 119 determines that a patient is beginning inspiration, the CPU 115 sends a signal to one or both of the control valves 107 and 109 to open the control valves to deliver therapeutic gas.

Depending on the particular NO administration regimen, the control valves 107 and 109 can operate in a number of different ways. For example, if one or more pulses of therapeutic gas are to be administered in a breath, the proportional control valve 107 can be set to a certain opening and the binary control valve 109 can be used to provide the pulses of therapeutic gas. In this way, the proportional control valve 107 may act as a variable sized orifice to control the flow through the binary control valve 109. The opening of the proportional control valve 107 may be increased or decreased from one breath to the next, depending on the flow rate desired for the binary control valve 109. In one example, a first breath may use the proportional control 107 valve at 75% of the maximum opening, and a subsequent breath may use the proportional control valve 107 at 50% of the maximum opening. This combines the advantages of both valves in that the flow rate can be varied with the proportional control valve 107, and at the same time the system utilizes the fast response time and precision of the binary control valve 109.

This operation of the proportional control valve 107 and the binary control valve 109 can be useful for many administration schedules. One such administration schedule is one that varies the amount of NO administered to the patient each breath. A desired total amount of drug can be set by a user, such as an amount of NO to be provided per kilogram of ideal body weight per hour (mg/kg IBW/hr). A patient's ideal body weight is a function of a patient's sex and height. The device adjusts the amount of drug given per breath so that the amount delivered is independent of the patient's respiratory rate. The binary and proportional control valve configuration in FIG. 1 can provide a larger range of doses per breath by allowing the flow rate to change, rather than solely relying on varying the time that the valve is open. This can be particularly important if the timing or duration of the NO pulse is critical. Accordingly, in some embodiments, one or more pulses of therapeutic gas are provided in the first half of inspiration or first third of inspiration.

The memory may store a set of machine-executable instructions (or algorithms) for calculating the desired volume of the gas pulse and the pulsing schedule to achieve a particular patient prescription. For example, if the patient's breathing rate and the cylinder concentration are known, then the CPU 115 can calculate how much volume of therapeutic gas needs to be administered each breath or set of breaths to provide the desired dosage of nitric oxide. The memory may also record the time that the binary control valve 109 is open during each pulse, so that future calculations can take into account how much nitric oxide has previously been administered.

In some embodiments, the memory may store a set of machine-executable instructions (or algorithms), when executed by the CPU 115, cause the delivery device to perform a method comprising: sensing inspiration of a patient with a trigger sensor, delivering a pulse of therapeutic gas containing nitric oxide to the patient during inspiration, monitoring the patient's respiratory rate or changes in the patient's respiratory rate, and varying the quantity (e.g. volume or mass) of therapeutic gas delivered in a subsequent breath. The machine-executable instructions may also comprise instructions for any of the other methods described herein.

The valve configuration in FIG. 1 can also be used for administration schedules that provide a constant pulse volume or dose each breath, i.e. mL/breath, nmol/breath, ng/breath, etc. Here, a single device can be used for patients with a wide range of dose requirements because the proportional control valve 107 can be used to set the flow rate or supply pressure to the binary control valve 109. Accordingly, even if the flow rate does not change during a single patient's therapy, the device can still provide a range of doses for mL/breath having the same pulse width (i.e. length of pulse) and one device can be used for patients having different prescriptions. Furthermore, it may be desirable to change a given patient's therapy amount from one mL/breath amount to a different mL/breath amount as the patient's respiratory pattern changes. For example, a patient may require one dose of mL/breath when awake and a higher dose of mL/breath when asleep so that there is not a large variation in amount of drug delivered per hour or other time period.

Thus, the combination of a binary control valve and a proportional control valve can widen the dosing range capability or provide more precise control of NO delivery pulse timing to a patient.

Figure 2:
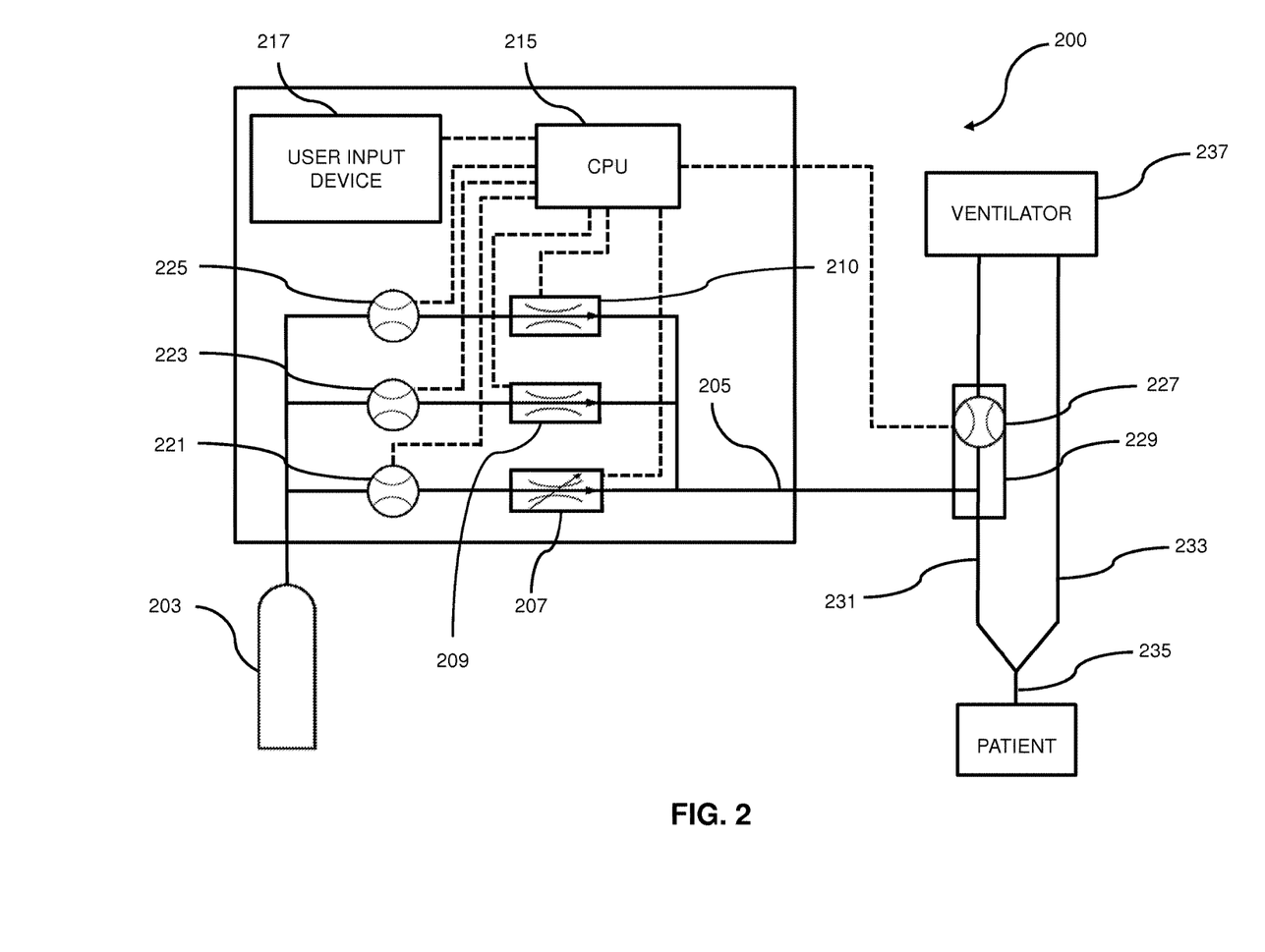
FIG. 2 illustrates a therapeutic gas delivery device having a proportional control valve and two binary control valves in parallel in accordance with one or more embodiments of the present invention.

The binary control valve and proportional control valve may also be in a parallel configuration, such as the one shown in FIG. 2. In FIG. 2, nitric oxide delivery device 200 has a proportional control valve in parallel with binary control valves 209 and 210. As with the device in FIG. 1, the nitric oxide delivery device 200 may be connected to a therapeutic gas source 203 that provides a supply of nitric oxide or a nitric oxide-releasing agent. Conduit 205 splits into three parallel flow paths, with each flow path having a different control valve (207, 209, 210) and its own flow sensor (221, 223, 225). More or fewer parallel flow paths may be used, and binary and proportional control valves may be combined in the same flow path. Furthermore, it is not necessary for each flow path to have its own flow sensor if a flow sensor is placed downstream of the convergence of the parallel flow paths or upstream of the divergence of the parallel flow paths.

A control system comprises a CPU 215 which may be in communication with each control valve (207, 209, 210) and each flow sensor (221, 223, 225). The CPU 215 may also be in communication with user input device 217. CPU 215 and user input device 217 may have any of the features described above for CPU 115 and user input device 117 in FIG. 1.

In FIG. 2, the nitric oxide delivery system 200 delivers therapeutic gas to a patient using a ventilator 237. Flow sensor 227 measures the flow of breathing gas from the ventilator 237 through the inspiratory limb 231 and sends a signal to CPU 215. CPU 215 then opens one or more control valves (207, 209, 210) to provide a flow of therapeutic gas through conduit 205, which is combined with the breathing gas in injector module 229. The CPU 215 provides a flow of therapeutic gas that is proportional (also known as ratiometric) to the breathing gas flow rate to provide a desired concentration of NO in the combined breathing gas and therapeutic gas. The combined therapeutic gas and breathing gas is then delivered to the patient via patient limb 235, and the patient's expiratory gases are carried through the expiratory limb 233 to the ventilator 237. Although flow sensor 227 is shown as within injector module 229, it may also be placed elsewhere in the inspiratory limb 231, such as upstream of the injector module 229. Also, instead of a flow sensor 227, the CPU 215 may receive a signal directly from the ventilator 237 indicating the flow of breathing gas from the ventilator 237.

The two configurations shown in FIG. 1 and FIG. 2 are only two examples of therapeutic gas delivery devices utilizing binary and proportional control valves. Other configurations can include, but are not limited to:
  a. two or more parallel flow paths, with each flow path having at least one binary control valve and at least one proportional control valve in series;
  b. two or more parallel flow paths, with one or more flow paths having at least one binary control valve and at least one proportional control valve in series and one or more other flow paths having only a binary control valve or only a proportional control valve;
  c. two or more parallel flow paths, with one or more flow paths having a binary control valve and one or more flows path having a proportional control valve; and
  d. a binary control valve in series with two or more proportional control valves in parallel flow paths.

One of ordinary skill in the art can envision other combinations of binary and proportional control valves in parallel and/or in series in accordance with the present invention. Furthermore, any of the configurations described herein may utilize a variable pressure regulator, either in addition to or as an alternative to a proportional control valve. For example, instead of a proportional control valve and a binary control valve in series, a variable pressure regulator placed upstream of the binary control valve may provide the same effect. Additionally, instead of configurations that have a binary control valve in parallel with a proportional control valve, two binary control valves may be in series with either one or both binary control valves having a variable pressure regulator upstream. A variable pressure regulator may also be used with a proportional control valve. In some embodiments, the variable pressure regulator comprises a proportional control valve and a pressure sensor.

In any of the configurations, if more than one binary control valve is used, they may have the same or different flow rates. It may be advantageous to have one binary control valve deliver at a higher flow rate than another binary control vale, such as having one binary control valve deliver at 6 L/min and another binary control valve deliver at 1 L/min. According to one or more embodiments, at least two binary control valves are used that have a flow rate ratio of the low flow rate valve to the high flow rate valve in the range from about 1:2 to about 1:10.

Similarly, if more than one proportional control valve is used, they may have the same or different flow ranges. For example, a first proportional control valve may have a flow rate range from 0.1 to 10 L/min and second proportional control valve may have a flow rate range from 0.005 to 1 L/min. Such an arrangement can maximize the accuracy of the therapeutic gas flow delivered by using the optimum working ranges for each proportional control valve, i.e. not using the extreme high end or the extreme low end of the working range for the valve.

In some embodiments, whether the control system will use one of the binary control valves (209, 210) or the proportional control valve (207) to deliver the therapeutic gas may depend on the therapeutic gas demand. The "therapeutic gas demand" is the amount of therapeutic gas required to provide the set NO in the combined flow of breathing gas and therapeutic gas. The therapeutic gas demand will vary based on the concentration of NO in the therapeutic gas, the set NO concentration and the flow rate of the breathing gas. If the cylinder concentration is 800 ppm NO and the breathing gas flow rate is 10 L/min, then approximately 0.5 L/min of therapeutic gas is required to provide a delivery concentration of 40 ppm. Accordingly, the therapeutic gas demand is 0.5 L/min for this combination of cylinder concentration, breathing gas flow rate and delivery concentration. When the therapeutic gas demand is a small fraction of the maximum therapeutic gas flow rate for the proportional control valve 207, the proportional control valve 207 may not deliver therapeutic gas with the same precision as with higher therapeutic gas demands. If the maximum therapeutic gas flow of the proportional control valve 207 is 6 L/min, then therapeutic gas demands less than 1 or 2% of this amount (i.e. less than 0.06 or 0.12 L/min) may not be accurately delivered with continuous flow through the proportional control valve 207. Thus, it may be advantageous to pulse either the proportional control valve 207 or one or more of the binary control valves (209, 210) at these low therapeutic gas demands. Although this pulsing technique may not result in continuous real-time therapeutic gas delivery that is proportional to the breathing gas flow, it can provide a "baseline" average concentration of NO. This pulsing technique may be especially useful when the ventilator 237 is outputting a low bias flow or when the nitric oxide delivery device is being used with a nasal cannula providing a low flow rate of oxygen to a patient.

Furthermore, in one or more embodiments, one or more proportional control valves may be used to deliver a pulse or pulses of NO. Such pulse or pulses of NO may be used to approximate a constant concentration dose of NO over a breath cycle. A device that uses such proportional control valve(s) to provide pulse(s) of NO may incorporate one or more binary control valves as described above, or may include only one or more proportional control valves for regulating the flow of NO. As described above, if more than one proportional control valve is used, they may have the same or different flow ranges. The device may also provide pulses of gas through the proportional valves at certain flow rates (such as lower flow rates) and provide a continuous flow of gas at other flow rates (such as higher flow rates).

Accordingly, in some embodiments, the CPU 215 uses the proportional control valve 207 at higher therapeutic gas demands and one or more of the binary control valves (209, 210) at lower therapeutic gas demands. In some embodiments, the delivery device 200 delivers a continuous flow of therapeutic gas through the proportional control valve 207 when the therapeutic gas demand is greater than 0.1% of the delivery range of the proportional control valve 207, such as when the therapeutic gas demand is greater than or equal to the following percentages of the delivery range: 0.5, 1, 2, 3, 4, 5, 6, 7, 8, 9, 10, 12, 15 or 20%. Likewise, in some embodiments, the delivery device delivers one or more pulses of therapeutic gas through the binary control valve 209 or 210 when the therapeutic gas demand is less than 20% of the delivery range of the proportional control valve 207, such as when the therapeutic gas demand is less than or equal to the following percentages of the delivery range: 15, 12, 10, 9, 8, 7, 6, 5, 4, 3, 2, 1, 0.5 or 0.1%. Alternatively, the delivery system 200 may pulse through the proportional control valve 207 when the demand is less than or equal to any of the previous percentages, or the delivery system may pulse through a binary control valve and proportional control valve combination that is in series when the therapeutic gas demand is low.

It is not necessary to use the nitric oxide delivery device 100 in FIG. 1 for single pulse per breath delivery (i.e. mg/kg IBW/hr or mL/breath) or use the nitric oxide delivery device 200 in FIG. 2 for constant concentration (either by repeatedly pulsing any of the control valves or continuously flowing through the proportional control valve). Indeed, any of these methods of nitric oxide delivery may use multiple binary and proportional control valves in parallel, in series, or combinations of both. Depending on the desired nitric oxide therapy, any of the devices described herein may have the appropriate breath trigger sensor for detecting the breath of a spontaneously breathing patient or may be adapted to use with a ventilator. Also, reference to "single pulse per breath" therapies encompasses methods that skip one or more breaths, in addition to methods that deliver a pulse of therapeutic gas every breath. It is also possible to use any of the devices described herein for either constant concentration dosing or pulse per breath dosing.

Another aspect of the current invention provides a method of administering a therapeutic or medical gas, the method comprising providing a therapeutic gas delivery device comprising at least one binary control valve and at least one proportional control valve and delivering therapeutic gas to the patient through one or more of the binary control valve and the proportional control valve. The therapeutic gas delivery device of this method may have any of the features previously described for therapeutic gas delivery devices having both binary and proportional control valves, such as having combinations of the valves in series, parallel or both. The therapeutic gas may comprise nitric oxide or a nitric oxide releasing agent. If the therapeutic gas comprises a nitric oxide-releasing agent, then it is preferably converted to nitric oxide prior to administering to the patient.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the methods and devices of the present invention without departing from the spirit and scope of the invention. Thus, it is intended that the present invention include modifications and variations that are within the scope of the appended claims and their equivalents.

What is claimed is:

1. A therapeutic gas delivery device comprising:
an inlet to connect to a source of therapeutic gas;
an outlet to connect to a device that introduces the therapeutic gas to a patient;
at least one binary control valve in fluid communication with the inlet and outlet that delivers a constant flow rate of the therapeutic gas when the upstream pressure is constant;
at least one variable pressure regulator in fluid communication with the binary control valve that controls the pressure upstream of the binary control valve, wherein the variable pressure regulator comprises a proportional control valve;
a control system that delivers the therapeutic gas through the binary control valve, wherein the control system is in communication with the proportional control valve and varies an opening size of the proportional control valve;
wherein the proportional control valve and binary control valve are simultaneously open during patient inspiration such that the proportional control valve controls the flow rate of the therapeutic gas through the binary control valve; and
wherein the control system is adapted to deliver the therapeutic gas to a patient in an amount proportional to a flow of breathing gas.

2. The therapeutic gas delivery device of claim 1, wherein the variable pressure controller further comprises a pressure sensor.

3. The therapeutic gas delivery device of claim 1, wherein the binary control valve is a first binary control valve and the therapeutic gas delivery device further comprises a second binary control valve in parallel to the first binary control valve.

4. The therapeutic gas delivery device of claim 3, wherein the first binary control valve and the second binary control valve deliver pulses of therapeutic gas at different flow rates.

5. The therapeutic gas delivery device of claim 4, wherein the ratio of the flow rate of the first binary control valve to the flow rate of the second binary control valve is in the range from about 1:2 to about 1:10.

6. The therapeutic gas delivery device of claim 3, wherein the control system delivers multiple pulses per breath through one or more of the first binary control valve and the second binary control valve.

7. The therapeutic gas delivery device of claim 1, wherein the device that introduces the therapeutic gas to the patient is in fluid communication with a ventilator.

8. The therapeutic gas delivery device of claim 1, wherein the device that introduces the therapeutic gas to the patient is a nasal cannula, an endotracheal tube or a face mask.

9. The therapeutic gas delivery device of claim 1, wherein the control system is adapted to provide a single pulse in a patient's breath.

10. The therapeutic gas delivery device of claim 1, further comprising at least one proportional control valve parallel to the binary control valve.

11. The therapeutic gas delivery device of claim 1, wherein the source of therapeutic gas comprises nitric oxide or a nitric oxide-releasing agent.

12. A method of administering a therapeutic gas to a patient, the method comprising:
receiving a flow of therapeutic gas to a therapeutic gas delivery device having at least one binary control valve that delivers a constant flow rate of the therapeutic gas when the upstream pressure is constant and at least one variable pressure regulator in fluid communication with the binary control valve that controls the pressure upstream of the binary control valve, wherein the variable pressure regulator comprises a proportional control valve;
measuring a flow of breathing gas; and
delivering therapeutic gas to the patient during inspiration through the binary control valve in an amount proportional to the flow of breathing gas, wherein the proportional control valve and binary control valve are simultaneously open during patient inspiration such that the proportional control valve controls the flow rate of the therapeutic gas through the binary control valve, and a control system in communication with the proportional control valve varies an opening size of the proportional control valve.

13. The method of claim 12, wherein the variable pressure controller further comprises a pressure sensor.

14. The method of claim 12, wherein the binary control valve is a first binary control valve and the therapeutic gas delivery device further comprises a second binary control valve in parallel to the first binary control valve.

15. The method of claim 14, wherein the first binary control valve and the second binary control valve deliver pulses of therapeutic gas at different flow rates.

16. The method of claim 15, wherein the ratio of the flow rate of the first binary control valve to the flow rate of the second binary control valve is in the range from about 1:2 to about 1:10.

17. The method of claim 12, further comprising sensing the beginning of the patient's inspiration and delivering one or more pulses of therapeutic gas to the patient during inspiration.

18. The method of claim 17, wherein at least one pulse is delivered in the first half of the patient's inspiration.

* * * * *